US006729801B1

(12) United States Patent
Walker et al.

(10) Patent No.: US 6,729,801 B1
(45) Date of Patent: May 4, 2004

(54) SYSTEM AND METHOD FOR DETECTING CONTAMINATION USING VEGETATION SAMPLING

(75) Inventors: John L. Walker, Chicago, IL (US); Barney W. Nashold, Mendota, IL (US); Jacqueline C. Burton, Chicago, IL (US)

(73) Assignee: University of Chicago, Chicago, IL (US)

(*) Notice: Subject to any disclaimer, the term of this patent is extended or adjusted under 35 U.S.C. 154(b) by 0 days.

(21) Appl. No.: 09/885,539

(22) Filed: Jun. 21, 2001

Related U.S. Application Data

(60) Provisional application No. 60/212,819, filed on Jun. 21, 2000.

(51) Int. Cl.⁷ .................................................. B09B 5/00
(52) U.S. Cl. ............................ 405/128.15; 405/128.1; 47/58.1
(58) Field of Search ...................... 405/128.1, 128.15, 405/128.45, 128.5, 128.7, 128.75

(56) References Cited

U.S. PATENT DOCUMENTS

| | | | |
|---|---|---|---|
| 5,927,005 A | * 7/1999 | Gardea-Torresdey et al. | 47/58.1 R |
| 6,145,244 A | * 11/2000 | Hodko et al. | 47/1.3 |
| 6,160,902 A | * 12/2000 | Dickson et al. | 382/110 |
| 6,313,374 B1 | * 11/2001 | KrishnaRaj et al. | 800/278 |

OTHER PUBLICATIONS

CMST–IP Mid Year Program Review, Table of Contents and Scetion 1.1—Expedited Site Characterization: Application and Continued Development of Rapid, Focused Site Characterized Methodology for Federal Facilities, 6 pages, Mar. 1993, from www.cmst.org.*

Doe, Office of Env Management, Office of Science and Technology, Innovative Technology Summary Report, DOE/EM–0420 "Expedited Site Characterization", OST reference #77, Dec. 1998, 21 pages, from www.OST.em.doe.gov under "Publications".*

DOE/OST May 1999 CMST Monthly Progress Report, EPCOT Section, 5 pages, May 1999, from www.cmst.org/cmst/Cmst–Cp_reports/May99/index.html.*

Survey Procedures manual, ORISE/ESSAP, Revision No. 11, Section 8.5 2 pages; table of contents, 5 pages; from www.orau.gov/essap/surveywhole,htm.© 1999.*

Walker, Nashold, and Burton, "Carbon Tetrachloride in Vegetation and its Application Expedited Site Characterization", Jun. 7–9, 1999, 10 Pages.*

Abstracts from www.ntis.gov/serch/product.asp?, NTIS order #s, DE940028910, DE94001700, DE95013717, DE99002653, and DE97054350, each 1 page, 5 pages total.

"Environmental Chemistry Team" from www.es.anl.gov/htmls/EnvChem.htm., 3 pages.

(List continued on next page.)

*Primary Examiner*—Robert J. Sandy
*Assistant Examiner*—Katherine Mitchell
(74) *Attorney, Agent, or Firm*—McDermott, Will & Emery

(57) ABSTRACT

A method for performing exploration of the vadose soil zone first obtains samples of the surface vegetation from a region, next the samples are analyzed to determine if a contaminant is present in any of the analyzed samples, and, finally, a determination is made if a vadose soil zone at that region is contaminated based on the analyzed samples. As a result of the contamination determination, further, more-detailed site characterization can be performed at only those regions that are contaminated.

22 Claims, 2 Drawing Sheets

OTHER PUBLICATIONS

Site Environmental Report for 1997, Preface, 2 pages; Chapter 9, Vegetation and Foodstuffs, 3 pages ; Chapter 1, Summary, 2 pages ; Chapter 5, Environmental Surveillance, 17 pages ; Chapter 17, Pre–Operational Monitoring, 2 pages; Sep. 1998.

Appendix A, Changes and Additions to the Vegetation Sampling and Analysis Plan, Fugitive Dust Study, Red Dog Mine, Alaska, from www.state,ak.us/local/akpages/ENV.CONSERV/press/reddog/documents/2001datarptappd.pdf , dated 2001.

References, Final Report of the 1999–2000 Vashon–Maury Island Soil Study, from www.metrokc.gov/health/hazards/vmrefs.htm ; 7 pages, last updated Jul. 2000, especially the references listed by ASARCO, Erdman et al., and Ratsch.*

Expedited Site Characterization: Application and Continued Development of Rapid, Focused Site Characterization Methodology for Federal Facilities, from www.cmst.org/publications.tech_summ_93/1.1html; 2 pages, 1993.*

Brush Fires and SSFL, BoeingCompany, Nov. 6, 2000; 4 pages.*

What is Quicksite®, ? From www.quicksite.anl.gov/quicksite/whatisqs.html; 2 pages; date unknown.*

* cited by examiner

SYSTEM AND METHOD FOR DETECTING CONTAMINATION USING VEGETATION SAMPLING

RELATED APPLICATIONS

This application relates to and claims priority from U.S. application Ser. No. 60/212,819 filed Jun. 21, 2000 entitled CARBON TETRACHLORIDE IN VEGETATION AND ITS APPLICATION TO EXPEDITED SITE CHARACTERIZATION, the disclosure of which is hereby incorporated in its entirety by reference.

FIELD OF THE INVENTION

The present invention relates to detecting environmental contamination and more particularly, to detecting such contamination in the vadose soil zone.

BACKGROUND OF THE INVENTION

The production, distribution, use, misuse, disposal, or accidental spills of many chemicals have polluted some environments to levels that threaten the health of humans, livestock, wildlife and, indeed, whole ecosystems. Most of these chemicals, or contaminants, are produced to improve human health, standards of living, and safety through advancements in manufacturing, agriculture and agribusiness, medicine, and to strengthen national defense. Ironically, their unplanned intrusions into the environment can have an adverse effect in direct contrast with their intended benefits.

In many countries, such as the United States, efforts to manage and measure the extent and level of the presence of these contaminants in the environment have resulted in many laws and regulations that prescribe, and proscribe, a variety of measures. Environmental site characterizations are usually one of the earliest steps in trying to identify and model pollution and contamination at a potential site. These site characterizations can include many aspects of the environments such as soil, air and water. Two common ways to characterize soil contamination include profiling the soil using core samples taken throughout the depth of a region and taking near-surface soil samples over a wide area.

Near-surface soil sampling has the significant drawback that soil at this depth is far from uniform in many, if not all, locations. The variability of soil type, texture and organic content impact both the reliability and the confidence of any characterization of soil contamination using this method. Soil profiles over a the entire depth of a soil layer are usually performed using grid drilling methods. Profiling the soil in this manner is very expensive, very slow, and invasive to the area.

Once an area has been determined to be contaminated, a number of methods for cleaning the site are available and many more are in the process of being developed. One area that has shown much promise and acceptance is using surface vegetation for bioremediation to assist in the cleaning-up of a site which is determined (such as through soil characterization) to be contaminated. Bioremediation describes several technologies and practices that take advantage of natural systems and processes to clean up pollution. These technologies entail the science of understanding natural processes that promote and accelerate destruction, transformation, removal, or stabilization of pollutants. The practice of bioremediation involves implementation and management of strategies that enhance these processes. Successful bioremediation strategies are those that are tailored to satisfy specific pollutant, site, public, regulatory, cost-effectiveness, and environmental-effectiveness considerations. Thus, bioremediation, while very useful, is a technology that is implemented only after a site is determined to be contaminated.

Independent of the above concerns, vegetation analysis has been used in the mining and petroleum industries to outline areas with near-surface enrichment of various compounds suggesting underlying deposits of interest. However, in these industries, the underlying deposits have had a time-frame of geological proportion to permeate upwards and affect both the soil and the vegetation growing in that soil. Also, these naturally occurring "marker" compounds are different than man-made contaminants which can render a site unhealthy. Specifically, these "marker" compounds are typically naturally occurring metals or relatively light hydrocarbons that are easy to detect.

There is a need, therefore, unmet by all the prior processes and procedures discussed above, for a method of quickly, inexpensively, and non-invasively determining areas of the vadose soil zone which are contaminated with contaminants that adversely impact the environment and that may have been in the sub-surface soil for only a relatively short period of time.

SUMMARY OF THE INVENTION

The present invention addresses and meets these and other needs by analyzing vegetation samples obtained from the surface of a region to determine whether the vadose soil zone of that region is contaminated. In particular, one aspect of the present invention relates to a method for performing exploration of the vadose soil zone by obtaining samples of the surface vegetation from a region, analyzing the samples to determine if a contaminant is present in the analyzed samples, and determining if a vadose soil zone at that region is contaminated based on the analyzed samples.

Another aspect of the present invention relates to a method for performing soil contaminant exploration which includes the step of determining the sub-surface contamination of a region by performing analysis on a plurality of surface vegetation samples of the region.

A still further aspect of the present invention relates to a method for performing soil contaminant exploration which includes the steps of determining the sub-surface contamination of a region by performing analysis on a plurality of surface vegetation samples of the region, and selecting that region for additional soil contamination characterization based on the analysis of the surface vegetation samples.

Yet another aspect of the present invention relates to a method for contaminant exploration that includes the step of determining whether or not an aquifer below a vadose soil zone of a region is contaminated by performing analysis on a plurality of surface vegetation samples from that region.

Still other objects and advantages of the present invention will become readily apparent from the following detailed description, simply by way of illustration of the best mode contemplated of carrying out the invention. As will be realized, the invention is capable of other and different embodiments and its several details are capable of modifications in various obvious respects, all without departing from the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF THE PREFERRED EMBODIMENT

To aid with the understanding of the present invention, exemplary embodiments are presented within the context of a specific environment involving detection of carbon tetrachloride. In general, however, the invention is applicable to other volatile organic compounds that collect in the tissue of live vegetation. For example, the present invention can be used to detect vadose soil zone contamination involving such compounds as, but not limited to, chloroform, 1,1-dichloroethane, 1,1-dichloroethene, 1,2-dichloroethane, trichloroethane, benzene, and toluene. It will be apparent, however, to one skilled in the art that the present invention may be practiced without these specific details. In other instances, well-known structures, devices, and processes are shown in block diagram form, herein, in order to avoid unnecessarily obscuring the present invention.

There are a number of areas of potential sub-surface soil contamination throughout the United States and the world for which detailed environmental analysis, characterizations, and health risk evaluations should, and could, be performed.

One example of such areas that involve relatively recent contamination sources includes a variety of United States Department of Agriculture (USDA) grain storage facilities operated between the 1950s and the 1970s. At these facilities, the USDA regularly stored and fumigated with a carbon tetrachloride based compound to control pests. Frequently, the carbon tetrachloride penetrated vertically into the soil beneath the storage sheds and Quonset huts on site and, thereby, contaminated the drinking water aquifers under the sites. Even though the surface structures at many of the sites have long been removed, the sub-surface soil may still contain remnant carbon tetrachloride, which acts as a continuing source of contamination.

Figure 1:
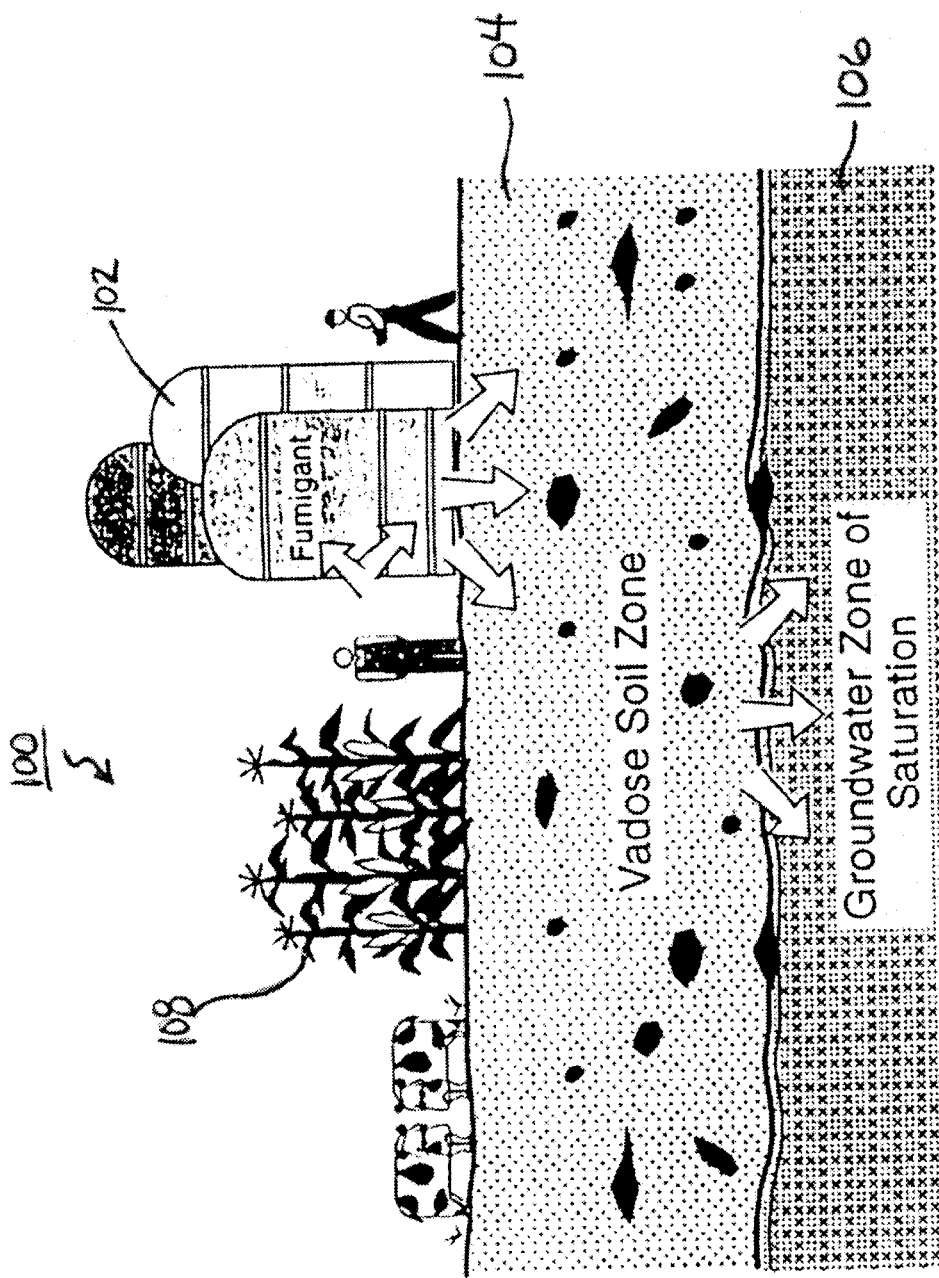
FIG. 1 illustrates an exemplary site with contamination sources.

FIG. 1 illustrates an exemplary USDA site while the fumigants and its storage facilities 102 were still on site 100. Surface vegetation 108 includes portions above the soil's top surface (e.g., leaves) and below the surface (e.g., roots). The vadose soil zone 104 is typically considered to be the soil between the surface and the water table. Below the vadose soil zone 104, therefore, is the groundwater zone of saturation 106.

Figure 2:
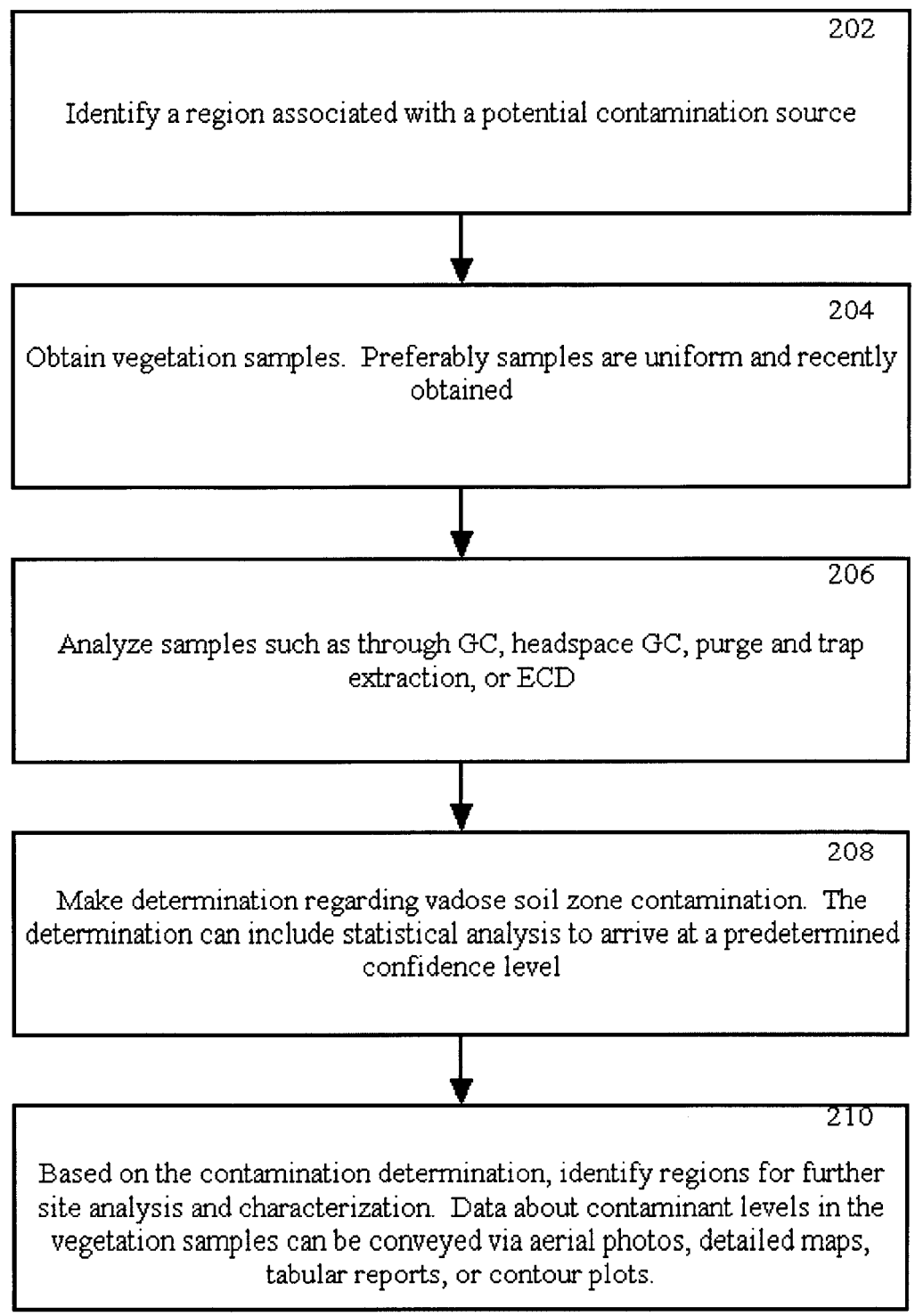
FIG. 2 a high-level flow diagram of a method for exploring soil contamination according to one embodiment of the present invention.

FIG. 2 illustrates a logical flow of exploring contamination of a subsurface region according to an embodiment of the present invention.

In an initial step 202, a region or regions at a site are identified that are related to a potential contamination source. Typically, as in the case of the exemplary USDA sites described above, some prior knowledge is usually available about those areas of the site where contaminants were introduced. For example, storage huts and other facilities may still be present, or only recently removed. Also, other visual indications or maps may be available to help locate the candidate regions where contamination, if present, is most likely to occur. Each of these regions can vary in size from around 100 square feet, such as for a small shed, to 300 square feet or more, such as for a Quonset hut or other large source. A site can contain multiple huts and, therefore, have a total size of 100,000 square feet or more.

Although the previously mentioned examples included prior knowledge about a site, there is no aspect of the present invention which prevents its methods from being used at sites for which there is no prior knowledge. For example, such a site could be separated into a grid of different regions and each region would then be considered as a possible contamination source and analyzed to determine the presence or absence of contamination.

The next step 204 of the flowchart, involves obtaining vegetation samples from the region(s) identified in step 202. In particular, these vegetation samples are obtained from live vegetation growing on the surface of the identified region. Such vegetation can include a wide variety of trees, grasses and legumes. Different parts of these different families of vegetation can also be used, such as leaves, roots, stalks, stems, etc. Dead grasses and dead portions of trees are not good candidate samples. In a preferred embodiment, the vegetation samples are collected during spring and early summer when the growth season for most vegetation is at its fullest.

While it is possible to practice the present invention by merely taking a single vegetation sample from a region, the resulting analysis and conclusions will be, at the very least, questionable and unreliable as there is no way to determine if the results are anomalous or not. In order to rely on the results from the samples, two or more contiguous samples should be observed with anomalous values; more so, the occurrence of three contiguous samples over an area, having anomalous values, essentially guarantees the presence of contamination.

Arranging the sampling points on a grid, for example, at a site is one method to ensure any anomalous results can be observed in two or more contiguous samples, thereby providing confidence in the determination that contaminants are present in the vegetation samples. In addition, the present invention contemplates within its scope grids of many sizes depending on the size of the site and the uniformity of its vegetative features. Furthermore, the grid does not need to be uniformly spaced across the entire site. Using prior knowledge about the location and the size of likely contaminant sources, the sample spacing in different sections of the grid can be reduced, or enlarged, as appropriate.

In the preferred embodiment, however, care is exercised when obtaining the samples to ensure that the different samples are uniform. As a result of emphasizing uniformity over other concerns, samples are not likely to be regularly spaced, or have a particular arrangement within a region. The uniformity of the samples involves a number of characteristics. For example, samples taken from trees should all be from the same type of tree. Similarly, samples taken from a grasses, should all be from the same grass. Within the set of grass samples, all the samples should be from the same part of the grass; likewise with the samples from trees. Each species of tree (or grass) accumulates the contaminant differently. Thus, anomalous data from samples within the same species can be recognized as contamination; while anomalous data from samples from different species may merely be a result of the different accumulation rates (rather than the absence of contamination).

For the same reason, in a particular region samples should not be mixed, if possible, between trees and grasses because certain species of trees can exhibit higher concentrations of the contaminants; instead, samples should be obtained from whatever type of vegetation that more uniformly covers that particular region. Accordingly, a site may have one region uniformly covered with trees and another region uniformly covered with grass. The samples from the first region should be from the trees and the samples from the second region should be from grass. However, when evaluating the data for anomalous contaminant concentration levels, each regions data which have to be separately considered and compared. Uniformity can also pertain to the size of the sample.

In a preferred embodiment, samples of some type of grass that is uniformly present at a site are obtained. Each of these samples is approximately one inch in length. More particularly, for each such sample there is about half and inch from below the ground's surface and about a half inch from above the ground's surface. Such a uniform sample will have a weight of about 3 to 4 grams, although as little as 0.5 grams is sufficient to perform analysis on. To preserve the sample in its best condition, the sample can be washed and packed in dry ice in the field. If such care is taken with grass samples, the samples can keep for approximately two months before the levels of contaminants begin to deteriorate to where the sample is no longer useful; although, using samples less than two weeks old is preferred.

Once the samples are obtained, they are analyzed to detect if contaminant levels in the samples are high enough to indicate a contamination problem. The analysis of the samples can be any of the many analysis methods known to those skilled in the art of chemical analysis. These analysis methods should be selected to accurately and precisely detect when a contaminant is present at more than a background level. For chemicals such as carbon tetrachloride and chloroform, for example, vegetation samples from controlled (i.e., very clean) sites may exhibit approximately 50 parts-per-trillion (ppt); while vegetation samples from most field locations would typically exhibit around 100 ppt. Analytical techniques should be selected that can accommodate these levels of contaminants. To aid in the analysis and later determinations, a baseline contaminant level for a region can be calculated by obtaining the same type of uniform samples from areas nearby the target region.

Purge and trap is a sample preparation technique that allows raw samples to be tested using gas chromatography and mass spectrometry. Purge and trap involves bubbling a high temperature carrier gas through a sample to strip volatile organics from it. Gas chromatography (GC) is the process of directing an organically rich gas through a chemically coated tube (or column) to separate the different species of chemicals in the gas. Determination of the type and amount of contaminant present is accomplished by measuring the time it takes vapors to exit the column, and measuring how much vapor exits at a given time. Mass spectrometry (MS) is a specialized analytical technique that breaks organic vapors into ions by bombarding molecules with electrons. The broken organic ions are attracted out of the ionization chamber by electrical charges, and a mass of exiting ions is measured to compare to the behavior of known chemicals.

Another analysis method, headspace GC makes use of the equilibrium between the volatile components of a liquid or solid sample and the surrounding gas phase in a sealed vessel, aliquots of the gas phase being injected into GC for analysis. According to the principle of headspace GC, the sample containing volatile components is placed in a sealed vial and conditioned until the volatile components partition into the vapor space above the sample and reach equilibrium; as a result, their concentration in the vapor phase is a function of the concentration of the original mixture. In this method, the sample is extracted by inert carrier gas with subsequent GC analysis. It is better to employ a gas as a solvent with its ideal solubility for every volatile component. Also, gas is normally available in higher purity than any liquid solvent, which avoids problems with trace impurity interferences.

The present invention contemplates within its scope the above methods of analysis as well as the many other methods known to one skilled in the art. In a preferred embodiment, however, headspace GC is used with a heating step of 95° C. for approximately two hours, followed by electron capture detection (ECD). This preferred method provides sufficient precision and accuracy to detect low contaminant levels of volatile organic compounds (e.g., carbon tetrachloride) that may have been in the vadose zone soil for 50 years or less.

As a result of the analysis of the samples, each sample has associated with it a contaminant concentration value. Based on the analysis results, a determination is made, in step 208, whether or not the vadose zone soil below a samples' region is contaminated. This contamination determination from the contamination concentration values of the analyzed samples relates to those results that are higher than a background fluctuation calculated for the analytical method. Accordingly, the samples' contamination concentration values can be analyzed so as to identify which vegetation samples show the presence of the contaminant and, thus, also indicate those areas with vadose soil zone contamination problems (i.e., the vadose zones below where the contaminated samples were obtained). The identification of vadose zones with contamination, also acts to identify which underlying aquifers are likely to be contaminated as well. As contamination in the vadose zone typically permeates down into the ground water, the aquifers underlying many contaminated vadose zones are, themselves, contaminated, as well as aquifers downgradient from the source.

In analyzing the concentration levels of different samples, the concentration values are compared to identify those data points which lay outside of the background fluctuations that are part of any analytical method. In the preferred analytical methods previously described, approximately 10% fluctuation can be expected in the sample concentration levels and, thus, recognizing this range as acceptable variation, samples can be evaluated to determine if they truly indicate a contamination condition or whether they merely indicate statistically insignificant variance. A background fluctuation of 10% is exemplary in nature only and other acceptable ranges of background fluctuation are contemplated that depend on many factors such as the samples' origins and the analytical methods chosen for use.

One reason that this view of the data is more useful than simply looking merely at the magnitude of the contaminant concentration value for a sample is that the contaminant concentration of a sample does not necessarily correlate directly with a contamination level in the vadose zone soil. For example, consider a very contaminated first site that may have had a top layer of soil removed or added at a time after the subsurface soil was originally contaminated, and a less contaminated second site that has had no surface treatment whatsoever. Because of the adulteration of the top soil level, the contamination concentration levels measured in vegetation samples at the first site will likely be less than the contamination levels measured in vegetation samples at the second site. Although, the first site, not the second, actually has more vadose soil zone contamination. However, if all other site characteristics are equal, or at least accounted and factored for, the samples' contaminant concentration levels can be used as a rough indication of the relative difference in vadose soil zone contamination levels.

After the determination is made regarding which regions and areas of a site likely have vadose soil zone contamination, these areas are identified, in step 210, for further, more detailed (and more expensive) soil characterization necessary to precisely and accurately model the distribution of the pollutant in the vadose zone soil. Stated another way, expensive testing can be avoided in those regions not indicating vadose zone contamination. For example, an aerial photograph (or a map from the same perspective) can be overlaid with circles, or points, that denote regions having vadose zone contamination. To convey additional information, these circles or dots can be visually distinct (e.g., color, line width, size, etc.) to reflect different ranges of the contamination levels of corresponding vegetation samples. Similarly, a contour map of a site can also be used to depict the contamination levels of the vegetation samples throughout the site. Equivalently, the data can be presented in a table or any of a multitude of other modes. Regardless of how the regions are identified, those regions indicating a high likelihood of subsurface contamination can be further evaluated and characterized.

Experiments and investigation using the present invention have shown that vegetation is an excellent sampling medium for the detection of carbon tetrachloride and other volatile organic compounds in the vadose soil zone. Vegetation provides uniform sample coverage of a site, and the analytical techniques used have a detection limit less than 100 parts-per-trillion with a precision of approximately ±10%. The results of the vegetation analysis provides the initial step in the characterization of the vadose zone and identifies the areas where concentrations of contaminants are most likely to remain in the deeper subsurface. This information helps to focus the more detailed feasibility studies in areas of greater subsurface soil contamination and, thus, provides a first-step exploratory techniques that is noninvasive, rapid, and inexpensive.

While this invention has been described in connection with what is presently considered to be the most practical and preferred embodiment, it is to be understood that the invention is not limited to the disclosed embodiment, but on the contrary, is intended to cover various modifications and equivalent arrangements included within the spirit and scope of the appended claims. The invention is capable of other and different embodiments and its several details are capable of modifications in various obvious respects, all without departing from the invention. Accordingly, the drawings and description are to be regarded as illustrative in nature, and not as restrictive.

What is claimed is:

1. A method for vadose zone soil contaminant exploration, comprising the steps of:

identify a geographical region;

obtaining a plurality of vegetation samples from living vegetation from a plurality of locations throughout the geographical region, each vegetation sample being associated with a location of the geographical region;

preserving the plurality of vegetation samples to reduce deterioration of the levels of any contaminants contained within the plurality of vegetation samples;

determining an amount of a contaminant within each sample using a predetermined method of analysis;

determining soil contamination at the location of the geographical region associated with a sample of the plurality of samples if the amount of contaminant within the sample is greater than a predetermined background fluctuation level of contaminate associated with the method of analysis; and performing an analysis of the amount of contaminant within each sample which is greater than the background fluctuation and the location of each sample to determine the vadose zone soil contamination of the geographic region.

2. The method according to claim 1, wherein the contamination is selected from the group consisting of carbon tetrachloride and chloroform.

3. The method according to claim 1, wherein the method of analysis is selected from the group consisting of gas chromatography, headspace gas chromatography, purge and trap extraction, electron capture detection, and mass spectrometric analysis.

4. The method according to claim 1, further comprising the step of:

selecting the geographical region for additional characterization of vadose zone soil contamination based on the analysis of the samples.

5. The method according to claim 1, wherein the contaminant is selected from the group consisting of carbon tetrachloride, chloroform, 1,1-dichloroethene, 1,1-dichloroethane, 1,2-dichloroethane, trichloroethane, benzene, toluene.

6. The method according to claim 1, further comprising the step of:

estimating a geographical range of contamination of the geographical region based on the analyzed samples.

7. The method according to claim 1, wherein the analyzing step further includes the step of:

determining if the contaminant is present at a level above substantially 100 parts-per-trillion.

8. The method according to claim 1, wherein the step of obtaining samples further includes the step of:

obtaining the plurality of samples such that each has substantially uniform size.

9. The method according to claim 1, wherein the step of obtaining samples further includes the step of:

obtaining the plurality of samples such that each has a first section from below ground level and a second section from above ground level, and the first section and the second section are substantially the same size.

10. The method according to claim 1, wherein the step of obtaining samples further includes the step of:

obtaining the plurality of samples such that each is of the same type vegetation.

11. The method according to claim 1, wherein the step of obtaining samples further includes the step of:

obtaining the plurality of samples from uniformly spaced locations within the region.

12. The method according to claim 1, wherein the step of obtaining samples further includes the step of:

obtaining 5 or more samples within the region.

13. The method according to claim 1, wherein the samples are selected from the group consisting of grasses, legumes, and trees.

14. The method according to claim 13, wherein the samples are obtained from a same part of he selected grasses, legumes, and trees.

15. The method according to claim 1, wherein the contaminant was introduced in the vadose zone soil within substantially 50 years of performing the analysis of the samples.

16. The method according to claim 1, wherein the step of determining further includes the step of:

performing analysis of the analyzed samples to satisfy a predetermined confidence level for the determination of contamination.

17. The method according to claim 1, wherein each sample is approximately one inch in length.

18. The method according to claim 1, wherein each sample weighs between substantially 0.5 grams and 4 grams.

19. The method according to claim 1, wherein the step of preserving the plurality of vegetation samples includes storing the plurality of samples with dry ice.

20. The method according to claim 19, wherein the plurality of samples are analyzed within two weeks of being obtained.

21. The method according to claim 1, wherein the step of obtaining samples includes collecting samples during a growth season for the vegetation.

22. The method according to claim 1, wherein the step of performing an analysis of the amount of contaminant within each sample which is greater than the background fluctuation and the location of each sample to determine the vadose zone soil contamination of the geographic region, determines the vadose zone soil contamination throughout the geographic region using a statistical analysis.

* * * * *

UNITED STATES PATENT AND TRADEMARK OFFICE
CERTIFICATE OF CORRECTION

PATENT NO. : 6,729,801 B1
DATED : May 4, 2004
INVENTOR(S) : John L. Walker et al.

It is certified that error appears in the above-identified patent and that said Letters Patent is hereby corrected as shown below:

Column 1,
Line 5, insert -- GOVERNMENT SUPPORT
  The United States Government has rights in this invention under Contract No. W-31-109-ENG-38 between the U.S. Department of Energy and the University of Chicago representing Argonne National Laboratory --.

Signed and Sealed this

Third Day of May, 2005

JON W. DUDAS
*Director of the United States Patent and Trademark Office*